(12) United States Patent
Ishihara

(10) Patent No.: US 9,417,188 B2
(45) Date of Patent: Aug. 16, 2016

(54) FLUORESCENCE OBSERVATION DEVICE

(71) Applicant: OLYMPUS CORPORATION, Tokyo (JP)

(72) Inventor: Yasushige Ishihara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 342 days.

(21) Appl. No.: 14/197,614

(22) Filed: Mar. 5, 2014

(65) Prior Publication Data

US 2014/0184790 A1 Jul. 3, 2014

Related U.S. Application Data

(63) Continuation of application No. PCT/JP2012/068586, filed on Jul. 23, 2012.

(30) Foreign Application Priority Data

Sep. 8, 2011 (JP) .................................. 2011-196217

(51) Int. Cl.
*G01N 21/64* (2006.01)
*A61B 1/00* (2006.01)
*A61B 1/04* (2006.01)
*G06T 5/00* (2006.01)

(52) U.S. Cl.
CPC ............ *G01N 21/64* (2013.01); *A61B 1/00009* (2013.01); *A61B 1/00039* (2013.01); *A61B 1/043* (2013.01); *G06T 5/00* (2013.01)

(58) Field of Classification Search
CPC .......... G01N 21/64; G06T 5/00; A61B 1/043; A61B 1/00009; A61B 1/00039
USPC ........................................................ 348/135
See application file for complete search history.

(56) References Cited

U.S. PATENT DOCUMENTS

2002/0161283 A1\* 10/2002 Sendai ................. A61B 5/0059
600/160
2004/0227069 A1\* 11/2004 Sendai .................. G06T 7/0012
250/252.1

(Continued)

FOREIGN PATENT DOCUMENTS

EP 2 526 853 A1 11/2012
JP 62-247232 A 10/1987

(Continued)

OTHER PUBLICATIONS

Extended Supplementary European Search Report dated Jan. 28, 2015 from related European Application No. 12 83 0529.9.

(Continued)

*Primary Examiner* — Andy Rao
*Assistant Examiner* — Jared Walker
(74) *Attorney, Agent, or Firm* — Scully, Scott, Murphy & Presser, PC

(57) ABSTRACT

Provided is a fluorescence observation device including: a processor configured to: extract, as a candidate region of interest, a region in a corrected fluorescence image that has a gradation value larger than a gradation-value threshold, the gradation-value threshold being set based on an average of gradiation values, a standard deviation, a first coefficient, and a second coefficient; receive a result, inputted by an observer, as to whether a candidate region of interest displayed on a display is a result of right indicating a determination by the observer that the candidate region of interest is a region of interest or a result of wrong indicating a determination by the observer that the candidate region of interest is not a region of interest; and set at least one of the first coefficient and the second coefficient so as to reflect the result inputted by the observer.

23 Claims, 8 Drawing Sheets

(56) References Cited

U.S. PATENT DOCUMENTS

| | | | | |
|---|---|---|---|---|
| 2010/0245551 A1* | 9/2010 | Morita | ............... | A61B 1/00009 348/68 |
| 2010/0245552 A1 | 9/2010 | Higuchi | | |
| 2010/0324371 A1 | 12/2010 | Ishihara | | |
| 2011/0211741 A1* | 9/2011 | Nakano | .............. | G01N 15/1434 382/128 |

FOREIGN PATENT DOCUMENTS

| JP | 3-58729 B2 | 9/1991 |
|---|---|---|
| JP | H05-028261 A | 2/1993 |
| JP | H07-129751 A | 5/1995 |
| JP | 2002-345739 A | 12/2002 |
| JP | 2006-043196 A | 2/2006 |
| JP | 2006-175052 A | 7/2006 |
| JP | 2009-226065 A | 10/2009 |
| WO | WO 2011/099363 A1 | 8/2011 |

OTHER PUBLICATIONS

International Search report dated Sep. 4, 2012 issued in PCT/JP2012/068586.

\* cited by examiner

FIG. 7

| No. | MEAN GRADATION VALUE m0 OF REGION OF INTEREST | DETERMI-NATION | THRESHOLD S0 | MEAN GRADATION VALUE | STANDARD DEVIATION | COEFFI-CIENT a | COEFFI-CIENT b | COEFFI-CIENT b0 | Y | N |
|---|---|---|---|---|---|---|---|---|---|---|
| 1 | 1650 | N | 1600 | 1500 | 100 | 1 | 1 | 1.5 | — | 1.5 |
| 2 | 2100 | Y | 1915 | 1600 | 210 | 1 | 1.5 | 2.38 | 2.38 | — |
| 3 | 1950 | Y | 1775 | 1400 | 250 | 1 | 1.5 | 2.2 | 2.2 | — |
| 4 | 2400 | Y | 2250 | 1800 | 300 | 1 | 1.5 | 2 | 2 | — |
| 5 | 1740 | N | 1700 | 1400 | 200 | 1 | 1.5 | 1.7 | — | 1.7 |
| 6 | 2100 | N | 2040 | 1800 | 150 | 1 | 1.6 | 2 | — | 2 |
| 7 | 2200 | Y | 2047 | 1700 | 200 | 1 | 1.73 | 2.5 | 2.5 | — |
| 8 | 1890 | N | 1843 | 1600 | 140 | 1 | 1.73 | 2.07 | — | 2.07 |
| 9 | 1920 | Y | 1873 | 1600 | 150 | 1 | 1.82 | 2.13 | 2.13 | — |
| 10 | 2000 | N | 1973 | 1700 | 150 | 1 | 1.82 | 2 | — | 2 |
| 11 | 1880 | N | 1726 | 1500 | 120 | 1 | 1.85 | 3.17 | — | 3.17 |
| 12 | 1910 | Y | 1907 | 1700 | 100 | 1 | 2.07 | 2.1 | 2.1 | — |
| 13 | 1900 | N | 1880 | 1600 | 140 | 1 | 2 | 2.14 | — | 2.14 |
| 14 | 1950 | Y | 1942 | 1400 | 260 | 1 | 2.08 | 2.12 | 2.12 | — |
| 15 | 2200 | Y | 2197 | 1800 | 200 | 1 | 198 | 2 | 2 | — |
| 16 | 1950 | Y | 1933 | 1600 | 170 | 1 | 1.96 | 2.06 | 2.06 | — |
| 17 | 1970 | N | 1966 | 1800 | 85 | 1 | 1.95 | 2 | — | 2 |
| 18 | 1950 | Y | 1911 | 1600 | 150 | 1 | 2.07 | 2.33 | 2.33 | — |

FIG. 8

| No. | AVE_Y(b0) | 0.9 × AVE_Y(b0) | AVE_N(b0) | NEW b |
|---|---|---|---|---|
| 1 | — | — | 1.5 | 1.5 |
| 2 | 2.38 | 2.14 | 1.5 | 1.5 |
| 3 | 2.29 | 2.06 | 1.5 | 1.5 |
| 4 | 2.19 | 197 | 1.5 | 1.5 |
| 5 | 2.19 | 1.97 | 1.6 | 1.6 |
| 6 | 2.19 | 1.97 | 1.73 | 1.73 |
| 7 | 2.27 | 2.04 | 1.73 | 1.73 |
| 8 | 2.27 | 2.04 | 1.82 | 1.82 |
| 9 | 2.24 | 2.02 | 1.82 | 1.82 |
| 10 | 2.24 | 2.02 | 1.85 | 1.85 |
| 11 | 2.24 | 2.02 | 2.07 | 2.07 |
| 12 | 2.22 | 2 | 2.07 | 2 |
| 13 | 2.22 | 2 | 2.08 | 2.08 |
| 14 | 2.2 | 1.98 | 2.08 | 1.98 |
| 15 | 2.18 | 1.96 | 2.08 | 1.96 |
| 16 | 2.17 | 1.95 | 2.08 | 1.95 |
| 17 | 2.17 | 1.95 | 2.07 | 2.07 |
| 18 | 2.18 | 1.96 | 2.07 | 1.96 |

FLUORESCENCE OBSERVATION DEVICE

CROSS-REFERENCE TO RELATED APPLICATIONS

This is a continuation of International Application PCT/JP2012/068586, with an international filing date of Jul. 23, 2012, which is hereby incorporated by reference herein in its entirety. This application claims the benefit of Japanese Patent Application No. 2011-196217, the content of which is incorporated herein by reference.

TECHNICAL FIELD

The present invention relates to a fluorescence observation device.

BACKGROUND ART

There are conventionally known fluorescence observation devices that acquire a reflected-light image and a fluorescence image of an observation target and divide the fluorescence image by the reflected-light image, thereby correcting variations in the brightness of the fluorescence image, which depend on the observation distance and the observation angle (for example, see PTLs 1, 2, and 3).

CITATION LIST

Patent Literature

{PTL 1}
Japanese Unexamined Patent Application, Publication No. Sho 62-247332
{PTL 2}
Japanese Examined Patent Application, Publication No. Hei 3-58729
{PTL 3}
Japanese Unexamined Patent Application, Publication No. 2006-175052

SUMMARY OF INVENTION

Technical Problem

The present invention is to provide a fluorescence observation device capable of reducing correction errors with respect to the influence of the observation distance and the observation angle and acquiring quantitative information of an object.

Solution to Problem

According to one aspect, the present invention provides a fluorescence observation device including: an illumination section that radiates excitation light and reference light onto an object; a fluorescence-image acquisition part that acquires a fluorescence image by capturing fluorescence produced in the object that has been irradiated with the excitation light from the illumination section; a reference-image acquisition part that acquires a reference image by capturing return light returning from the object that has been irradiated with the reference light from the illumination section; a corrected-fluorescence-image generation part that corrects the fluorescence image acquired by the fluorescence-image acquisition part by using the reference image acquired by the reference-image acquisition part, thus generating a corrected fluorescence image; a threshold setting part that sets a gradation-value threshold based on an average of gradation values of the entire corrected fluorescence image generated by the corrected-fluorescence-image generation part, a standard deviation of the gradation values, a first coefficient related to weighting of the average of the gradation values of the entire corrected fluorescence image, and a second coefficient related to weighting of the standard deviation of the gradation values; an extraction part that determines and extracts, as a region of interest, a region in the corrected fluorescence image that has a gradation value larger than the gradation-value threshold set by the threshold setting part; a display section that displays the region of interest extracted by the extraction part and the reference image in association with each other; and a right/wrong input section through which an observer inputs a result as to whether the determination of the region of interest displayed on the display section, made by the extraction part, is right or wrong, in which the threshold setting part sets at least one of the first coefficient and the second coefficient so as to reflect the input result input through the right/wrong input section.

According to the above-described aspect, when the excitation light emitted from the illumination section is radiated onto the object, the fluorescence-image acquisition part acquires a fluorescence image of fluorescence produced in the object. When the reference light emitted, together with the excitation light, from the illumination section is radiated onto the object, the reference-image acquisition part acquires a reference image of return light thereof. Then, the corrected-fluorescence-image generation part corrects the fluorescence image of the identical object with the reference image thereof, thereby generating a corrected fluorescence image in which the fluorescence intensity change that depends on the observation distance and the observation angle has been reduced.

When the display section displays a region that has a gradation value exceeding the gradation-value threshold, which is determined and extracted as a region of interest from the generated corrected fluorescence image by the extraction part, in association with the reference image.

In this state, when the observer viewing the displayed image inputs, through the right/wrong input section, a result indicating that the determination of the region of interest made by the extraction part is right or wrong, the threshold setting part sets at least one of the first coefficient and the second coefficient so as to reflect that input result. Then, a new gradation-value threshold is set based on the average of gradation values of the entire corrected fluorescence image, the standard deviation of the gradation values thereof, and the set at least one of the first coefficient and the second coefficient.

In the above-described aspect, the corrected-fluorescence-image generation part may divide the fluorescence image by the reference image.

In the above-described aspect, the threshold setting part may set one of the first coefficient and the second coefficient to a fixed value and may maintain or reduce the other coefficient when a result indicating that the determination is right is input through the right/wrong input section.

If the observer inputs a result indicating that the determination of the region of interest made by the extraction part is right, when the difference between the gradation value of the region of interest and the gradation-value threshold is significantly large, that gradation-value threshold is appropriate. Therefore, in this case, by fixing one of the first coefficient and the second coefficient and maintaining the other coefficient, specifically, by maintaining the gradation-value threshold, there is a high possibility that a necessary region of interest will be extracted without being overlooked, in the next round of region-of-interest extraction, as well.

On the other hand, when the difference between the gradation value of the region of interest and the gradation-value threshold is small, there is a possibility that it will be determined that a region having a gradation value lower than that gradation-value threshold should be extracted as a region of interest, in subsequent rounds of extraction. Therefore, in this case, by fixing one of the first coefficient and the second coefficient and reducing the other coefficient to reduce the gradation-value threshold, it is possible to extract a region having a gradation value lower than the current gradation-value threshold as a region of interest, at the next round of region-of-interest extraction.

In the above-described aspect, the threshold setting part may maintain the other coefficient when the gradation value of the region of interest is larger than an upper gradation-value threshold that is higher than the gradation-value threshold by a predetermined rate and may reduce the other coefficient when the gradation value of the region of interest is lower than the upper gradation-value threshold.

In the above-described aspect, the threshold setting part may set one of the first coefficient and the second coefficient to a fixed value and may increase the other coefficient when a result indicating that the determination is wrong is input through the right/wrong input section.

If the observer inputs a result indicating that the determination of the region of interest made by the extraction part is wrong, there is a low possibility that it will be determined that a region having a gradation value smaller than the gradation-value threshold that was used to extract that region of interest should be extracted as a region of interest in subsequent rounds of extraction, as well. In this case, by fixing one of the first coefficient and the second coefficient and increasing the other coefficient to increase the gradation-value threshold.

In the above-described aspect, the threshold setting part may calculate the gradation-value threshold by the following equation:

$$S0 = a \times m + b \times \sigma$$

where
S0 indicates the gradation-value threshold,
a indicates the first coefficient,
b indicates the second coefficient,
m indicates the average of the gradation values of the entire corrected fluorescence image, and
$\sigma$ indicates the standard deviation of the gradation values of the entire corrected fluorescence image.

In the above-described aspect, the extraction part may calculate an average of gradation values of the extracted region, and the threshold setting part may calculate a third coefficient based on the average of the gradation values of the extracted region; a storage part that stores, when the region of interest is extracted by the extraction part and when a determination of the region of interest made by the observer is input through the input section, the determination result and the third coefficient in association with each other may be provided; and, when a result indicating that the determination of a new region of interest is right is input through the right/wrong input section, the threshold setting part may set, as a new first coefficient, the smaller of the current first coefficient and a lower coefficient that is lower, by a predetermined rate, than an average value of previous third coefficients stored in the storage part in association with the input determination result.

In the above-described aspect, the extraction part may calculate an average of gradation values of the extracted region, and the threshold setting part may calculate a third coefficient based on the average of the gradation values of the extracted region; a storage part that stores, when the region of interest is extracted by the extraction part and when a determination of the region of interest made by the observer is input through the input section, the determination result and the third coefficient in association with each other may be provided; and, when a result indicating that the determination of a new region of interest is right is input through the right/wrong input section, the threshold setting part may set, as a new second coefficient, the smaller of the current second coefficient and a lower coefficient that is lower, by a predetermined rate, than an average value of previous third coefficients stored in the storage part in association with the input determination result.

In the above-described aspect, the extraction part may calculate an average of gradation values of the extracted region, and the threshold setting part may calculate a third coefficient based on the average of the gradation values of the extracted region; a storage part that stores, when the region of interest is extracted by the extraction part and when a determination of the region of interest made by the observer is input through the input section, the determination result and the third coefficient in association with each other may be provided; and, when a result indicating that the determination of a new region of interest is right is input through the right/wrong input section, the threshold setting part may calculate a standard deviation of the previous third coefficients stored in the storage part in association with the input determination result and may set, as a new first coefficient, the smaller of the current first coefficient and a lower coefficient that is obtained by subtracting the calculated standard deviation of the third coefficients from an average value of the previous third coefficients stored in the storage part.

In the above-described aspect, the extraction part may calculate an average of gradation values of the extracted region, and the threshold setting part may calculate a third coefficient based on the average of the gradation values of the extracted region; a storage part that stores, when the region of interest is extracted by the extraction part and when a determination of the region of interest made by the observer is input through the input section, the determination result and the third coefficient in association with each other may be provided; and, when a result indicating that the determination of a new region of interest is right is input through the right/wrong input section, the threshold setting part may calculate a standard deviation of the previous third coefficients stored in the storage part in association with the input determination result and may set, as a new second coefficient, the smaller of the current second coefficient and a lower coefficient that is obtained by subtracting the calculated standard deviation of the third coefficients from an average value of the previous third coefficients stored in the storage part.

In the above-described aspect, when a result indicating that the determination made by the extraction part is wrong is input through the right/wrong input section, the threshold setting part may set, as a new first coefficient, the average value of the previous third coefficients stored in the storage part in association with the input determination result.

In the above-described aspect, when a result indicating that the determination made by the extraction part is wrong is input through the right/wrong input section, the threshold setting part may set, as a new second coefficient, the average value of the previous third coefficients stored in the storage part in association with the input determination result.

In the above-described aspect, the threshold setting part may calculate the third coefficient by the following equation:

$$a0 = (m0 - b \times \sigma)/m$$

where a0 indicates the third coefficient, m0 indicates the average of the gradation values of the extracted region, b indicates the second coefficient, σ indicates the standard deviation of the gradation values of the entire corrected fluorescence image, and m indicates the average of the gradation values of the entire corrected fluorescence image.

In the above-described aspect, the threshold setting part may calculate the third coefficient by the following equation:

$$b0 = (m0 - a \times m)/\sigma$$

where b0 indicates the third coefficient, m0 indicates the average of the gradation values of the extracted region, a indicates the first coefficient, m indicates the average of the gradation values of the entire corrected fluorescence image, and σ indicates the standard deviation of the gradation values of the entire corrected fluorescence image.

In the above-described aspect, the display section may display the region of interest and the reference-light image in a superimposed manner.

In the above-described aspect, the extraction part may extract, as the region of interest, a region whose pixel count is larger than a pixel count threshold among regions that have gradation values exceeding the gradation-value threshold.

In the above-described aspect, a storing part that stores the gradation value of the region of interest and information about a previous determination result in association with each other may be further included, and the display section may read, for each region of interest, information about the previous determination result associated with the gradation value of that region of interest from the storing part and may display the information.

BRIEF DESCRIPTION OF DRAWINGS

FIG. 7 is a diagram for explaining data stored in a storing part of the fluorescence observation device shown in FIG. 6.

FIG. 8 is a diagram showing a change in a coefficient set by the fluorescence observation device according to the second embodiment of the present invention.

DESCRIPTION OF EMBODIMENTS

First Embodiment

A fluorescence observation device according to a first embodiment of the present invention will be described below with reference to the drawings.

Figure 1:
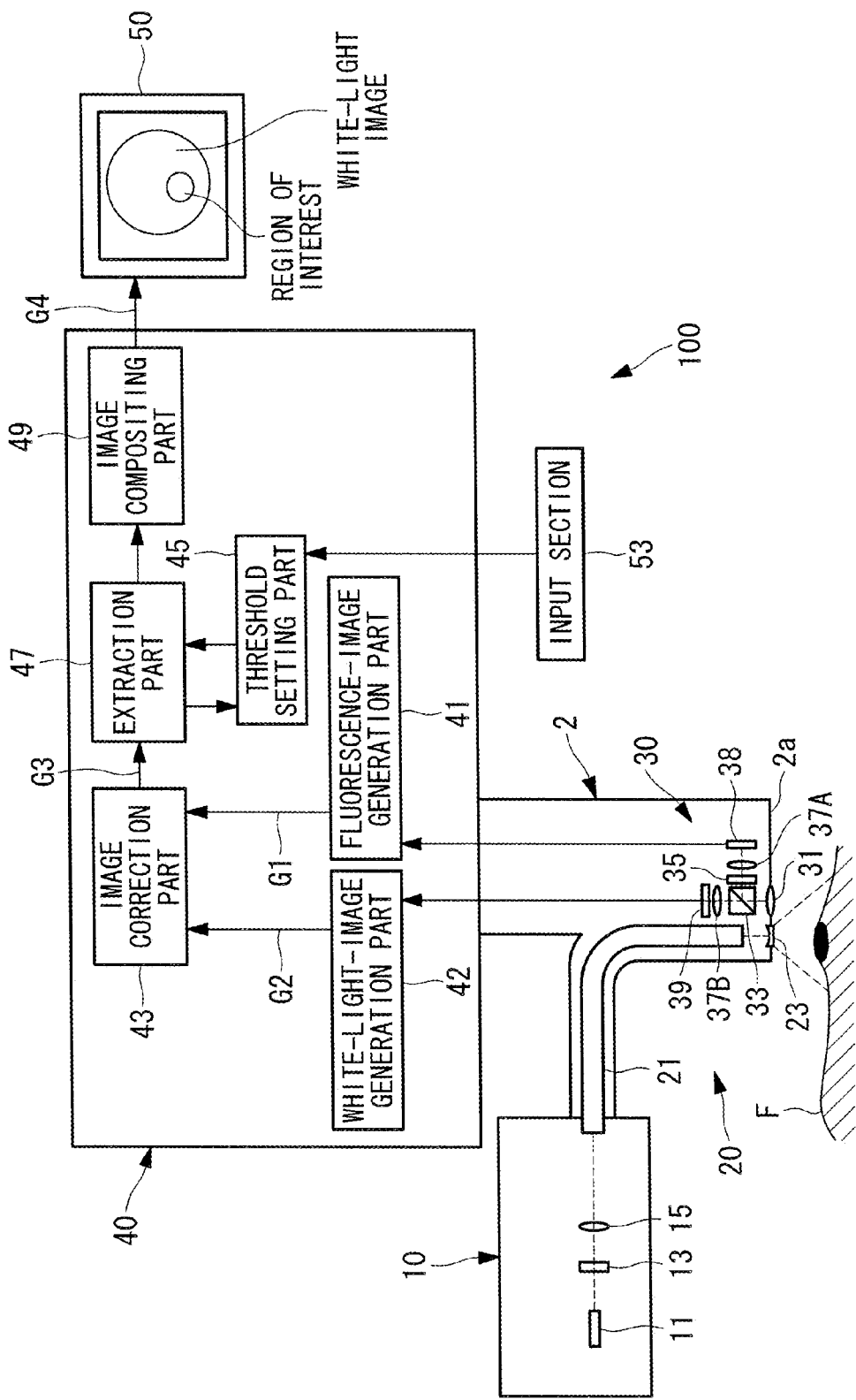
FIG. 1 is a configuration diagram showing, in outline, a fluorescence observation device according to a first embodiment of the present invention.

As shown in FIG. 1, a fluorescence observation device 100 according to this embodiment includes an elongated insertion portion 2 that is to be inserted into a body, a light source (illumination section) 10 that emits excitation light and illumination light, an illumination unit (illumination section) 20 that radiates the excitation light and the illumination light emitted from the light source 10 onto an object F from a distal end 2a of the insertion portion 2, an image acquisition unit 30 that is located in a distal end portion of the insertion portion 2 and that acquires image information of living tissue, which is the object F, an image processing section 40 that processes the image information acquired by the image acquisition unit 30, a monitor (display section) 50 that displays an image processed by the image processing section 40, and an input section (right/wrong input section) 53 through which an observer performs input.

The light source 10 includes a xenon lamp 11 that emits illumination light, an excitation light filter 13 that cuts out excitation light and white light (reference light) from the light emitted from the xenon lamp 11, and a coupling lens 15 that converges the excitation light and the white light cut out by the excitation light filter 13. The excitation light filter 13 cuts out excitation light and white light in a wavelength band from 400 to 740 nm, for example.

The illumination unit 20 includes a light guide fiber 21 that is located over the entire length of the insertion portion 2 in the longitudinal direction and an illumination optical system 23 that is located at the distal end 2a of the insertion portion 2.

The light guide fiber 21 guides the excitation light and the white light converged by the coupling lens 15 to the distal end 2a of the insertion portion 2.

The illumination optical system 23 spreads out the excitation light and the white light guided by the light guide fiber 21 to radiate them onto the object F.

The image acquisition unit 30 includes an objective lens 31 that collects return light returning from the object F onto which the excitation light and the white light have been radiated by the illumination unit 20 and a dichroic mirror 33 that splits the return light collected by the objective lens 31 into the respective wavelengths.

The objective lens 31 is located at the distal end 2a of the insertion portion 2 in parallel with the illumination optical system 23.

Of the return light, the dichroic mirror 33 reflects light having an excitation wavelength or longer (excitation light and fluorescence) and transmits white light (return light) having a wavelength shorter than the excitation wavelength.

The image acquisition unit 30 includes an excitation-light cut filter 35 that cuts off excitation light and transmits only fluorescence (for example, near-infrared fluorescence), of the excitation light and the fluorescence reflected in the dichroic mirror 33; a focusing lens 37A that focuses the fluorescence transmitted through the excitation-light cut filter 35; a fluorescence capturing part 38 that captures the fluorescence focused by the focusing lens 37A; a focusing lens 37B that focuses the white light transmitted through the dichroic mirror 33; and a white-light capturing part 39 that captures the white light focused by the focusing lens 37B.

The excitation-light cut filter 35 transmits only fluorescence in a wavelength band from 760 to 850 nm, for example.

The fluorescence capturing part 38 is, for example, a highly-sensitive monochrome CCD for fluorescence. The fluorescence capturing part 38 acquires fluorescence image information by capturing fluorescence.

The white-light capturing part 39 is, for example, a color CCD for white light and includes a mosaic filter (not shown). The white-light capturing part 39 acquires white-light image information by capturing white light.

The image processing section 40 includes a fluorescence-image generation part (fluorescence-image acquisition part) 41 that generates a fluorescence image G1 from the fluorescence image information acquired by the fluorescence capturing part 38; a white-light-image generation part (reference-image acquisition part) 42 that generates a white-light image G2 from the white-light image information acquired by the white-light capturing part 39; an image correction part (corrected-fluorescence-image generation part) 43 that corrects the fluorescence image G1 with the white-light image G2 to generate a corrected fluorescence image G3; a threshold setting part 45 that sets a threshold (gradation-value threshold) S0 for a gradation value in the corrected fluorescence image G3; an extraction part 47 that extracts, from the corrected fluorescence image G3, a region having a gradation value equal to or larger than the threshold S0 set by the threshold setting part 45, as a region of interest; and an image compositing part 49 that generates a superimposed image G4 by superimposing the region of interest extracted by the extraction part 47 on the white-light image G2.

The image correction part 43 divides the fluorescence image G1 of the identical object F by the white-light image G2 thereof, thereby correcting the fluorescence image G1. Thus, the corrected fluorescence image G3, in which the fluorescence intensity change that depends on the observation distance and the observation angle in the fluorescence image G1 has been reduced, is generated. The image correction part 43 sends the generated corrected fluorescence image G3 to the extraction part 47 and the threshold setting part 45 and also sends the white-light image G2 and the corrected fluorescence image G3 to the image compositing part 49 via the extraction part 47.

The extraction part 47 measures the area (pixel count) P of the extracted region, and, if the area P has a certain size or larger, specifically, if the area P is larger than a predetermined pixel count threshold P0, determines the region to be a region of interest. The extraction of a region of interest that has a gradation value equal to or larger than the threshold S0 and that has a pixel count larger than the pixel count threshold P0 may be performed by either of the following methods: a method in which a region having a larger pixel count is extracted from regions first extracted based on the gradation value, and a method in which a region having a larger gradation value is extracted from regions first extracted based on the pixel count.

The extraction part 47 sends information about the extracted region of interest to the threshold setting part 45 and the image compositing part 49. The extraction part 47 calculates the average of gradation values of pixels in the extracted region of interest (hereinafter referred to as "the average gradation value of the region of interest") m0 and sends it to the threshold setting part 45.

The image compositing part 49 generates the superimposed image G4 by superimposing, on the white-light image G2, the corrected fluorescence image G3 generated by the image correction part 43, from which the background other than the region of interest extracted by the extraction part 47 has been removed. The image compositing part 49 sends the generated superimposed image G4 to the monitor 50.

The monitor 50 displays the superimposed image G4 generated by the image compositing part 49. The monitor 50 also displays a selection message for urging the observer, such as a doctor, to input a determination as to whether the region of interest, extracted by the extraction part 47, in the displayed superimposed image G4 is the right region with a suspected lesion. An example of the displayed selection message for urging an input is, for example, "Does the region of interest have a lesion (Y/N)?".

The observer visually confirms the superimposed image G4 displayed on the monitor 50, determines whether the region of interest is a region with a suspected lesion, from morphological characteristics, such as the shape and the color, of an observed site displayed on the corrected fluorescence image G3 or from the size and the brightness of the region of interest, and inputs a determination result through the input section 53.

The input section 53 is, for example, a desired input device, such as a keyboard or a mouse.

The determination result input by the observer through the input section 53 is input to the threshold setting part 45.

The threshold setting part 45 calculates the average m of gradation values of the pixels in the corrected fluorescence image G3 (the average of gradation values in the entire corrected fluorescence image G3; hereinafter referred to as "the average gradation value of the entire corrected fluorescence image G3") and a standard deviation $\sigma$ of gradation values of the pixels in the corrected fluorescence image G3 (the standard deviation of the gradation values in the entire corrected fluorescence image G3; hereinafter referred to as "standard deviation of the entire corrected fluorescence image G3"), by using the following Equations (1) and (2).

Equation 1

$$m = \frac{n_1 \times m_1 + n_2 \times m_2}{n_1 + n_2} \qquad (1)$$

In Equation (1), $m_1$ indicates the average of gradation values of pixels representing the background;

$m_2$ indicates the average of gradation values of pixels representing a lesion;

$n_1$ indicates the total number of the pixels representing the background; and $n_2$ indicates the total number of the pixels representing the lesion.

Equation 2

$$\begin{aligned}\sigma^2 &= \langle x^2 \rangle - m^2 \\ &= \frac{n_1 \langle x_1^2 \rangle + n_2 \langle x_2^2 \rangle}{n_1 + n_2} - m^2 \\ &= \frac{n_1 (\sigma_1^2 + m_1^2) + n_2 (\sigma_2^2 + m_2^2)}{n_1 + n_2} - m^2\end{aligned} \qquad (2)$$

In Equation (2), $\langle x^2 \rangle$ indicates the average of the squares of gradation values of the entire corrected fluorescence image G3;

$\langle x_1^2 \rangle$ indicates the average of the squares of gradation values of background;

$\langle x_2^2 \rangle$ indicates the average of the squares of gradation values of a lesion;

$\sigma_1$ indicates the standard deviation of gradation values of pixels representing the background; and $\sigma_2$ indicates the standard deviation of gradation values of pixels representing the lesion.

The threshold setting part 45 sets the threshold S0 based on the sum of the average gradation value m and the standard deviation $\sigma$ of the entire corrected fluorescence image G3, as indicated by Equation (3).

$$S0 = a \times m + b \times \sigma \quad (3)$$

In Equation (3), a indicates a coefficient (first coefficient); and b indicates a coefficient (second coefficient).

The threshold setting part 45 sets the coefficient (first coefficient) a and the coefficient (second coefficient) b so as to reflect the input result input through the input section 53, thus setting a new threshold S0.

Specifically, if the observer determines that "the region of interest has a suspected lesion (Y)", that is, "the threshold used by the extraction part 47 to extract the region of interest is right", (hereinafter referred to as "Y determination"), the threshold setting part 45 determines whether an average gradation value m0 of the region of interest input from the extraction part 47 falls below an upper threshold (upper gradation-value threshold) that is higher than the threshold S0 by a predetermined rate.

Then, if the average gradation value m0 of the region of interest falls below the upper threshold, the threshold setting part 45 reduces the values of the coefficients a and b, and, if the average gradation value m0 of the region of interest exceeds the upper threshold, the threshold setting part 45 maintains the values of the coefficients a and b.

In this embodiment, it is assumed that the coefficient a is fixed to 1, and the coefficient b is updated as needed, in the following description.

For example, the upper threshold is set to the value obtained by $1.1 \times S0$.

When $m0 < 1.1 \times S0$ is established, the coefficient b is updated to the value obtained by $0.9 \times b$.

When $m0 \geq 1.1 \times S0$ is established, the value of the coefficient b is maintained.

On the other hand, if the observer determines that "the region of interest does not have a suspected lesion (N)", that is, "the threshold S0 used by the extraction part 47 to extract the region of interest is wrong", (hereinafter referred to as "N determination"), the threshold setting part 45 increases the value of the coefficient b.

For example, the coefficient b is updated to the value obtained by $1.1 \times b$.

The threshold S0 set by the threshold setting part 45 is input to the extraction part 47 and is set in the extraction part 47 as a new threshold S0. Thus, when a new corrected fluorescence image G3 is generated, a region of interest is extracted by using the new threshold S0. While repeating a similar procedure, the threshold setting part 45 sets a threshold S0 for each corrected fluorescence image G3.

The advantageous effect of the thus-configured fluorescence observation device 100 of this embodiment will now be described.

In order to observe living tissue, which is the object F, in the body of a patient by using the fluorescence observation device 100 of this embodiment, the insertion portion 2 is inserted into the body of the patient so that the distal end 2a thereof opposes the object F. Then, the light source 10 is actuated to emit excitation light and illumination light, and the coupling lens 15 makes the excitation light and illumination light enter the light guide fiber 21. The excitation light and the illumination light guided by the light guide fiber 21 and reaching the distal end 2a of the insertion portion 2 are spread out by the illumination optical system 23 and are radiated onto the object F.

A fluorescent substance contained in the object F is excited by the excitation light to produce fluorescence, and the white light and part of the excitation light are reflected on the surface of the object F. These fluorescence, white light, and excitation light return to the distal end 2a of the insertion portion 2 from the object F and are partially collected by the objective lens 31.

The fluorescence, the white light, and the excitation light collected by the objective lens 31 are split into the respective wavelengths by the dichroic mirror 33. Specifically, at the dichroic mirror 33, the excitation light and the fluorescence, which have excitation wavelengths or longer, are reflected, and the white light, which has a wavelength shorter than the excitation wavelength, is transmitted.

Of the excitation light and the fluorescence reflected at the dichroic mirror 33, the excitation light is cut by the excitation-light cut filter 35, and only the fluorescence is focused by the focusing lens 37A and is captured by the fluorescence capturing part 38. Thus, the fluorescence capturing part 38 acquires fluorescence image information of the object F.

The white light transmitted through the dichroic mirror 33 is focused by the focusing lens 37B and is captured by the white-light capturing part 39. Thus, the white-light capturing part 39 acquires white-light image information of the object F.

The fluorescence image information and the white-light image information may be acquired in any order or may be acquired at the same time.

The fluorescence image information acquired by the fluorescence capturing part 38 and the white-light image information acquired by the white-light capturing part 39 are sent to the image processing section 40. In the image processing section 40, the fluorescence image information is input to the fluorescence-image generation part 41 where a fluorescence image G1 is generated, and the white-light image information is input to the white-light-image generation part 42 where a white-light image G2 is generated.

The fluorescence image G1 generated by the fluorescence-image generation part 41 and the white-light image G2 generated by the white-light-image generation part 42 are sent to the image correction part 43, and a corrected fluorescence image G3 is generated therein by dividing the fluorescence image G1 by the white-light image G2. The generated corrected fluorescence image G3 is sent from the image correction part 43 to the extraction part 47 and the threshold setting part 45. The white-light image G2 and the corrected fluorescence image G3 are sent from the image correction part 43 to the image compositing part 49 via the extraction part 47.

Figure 2:
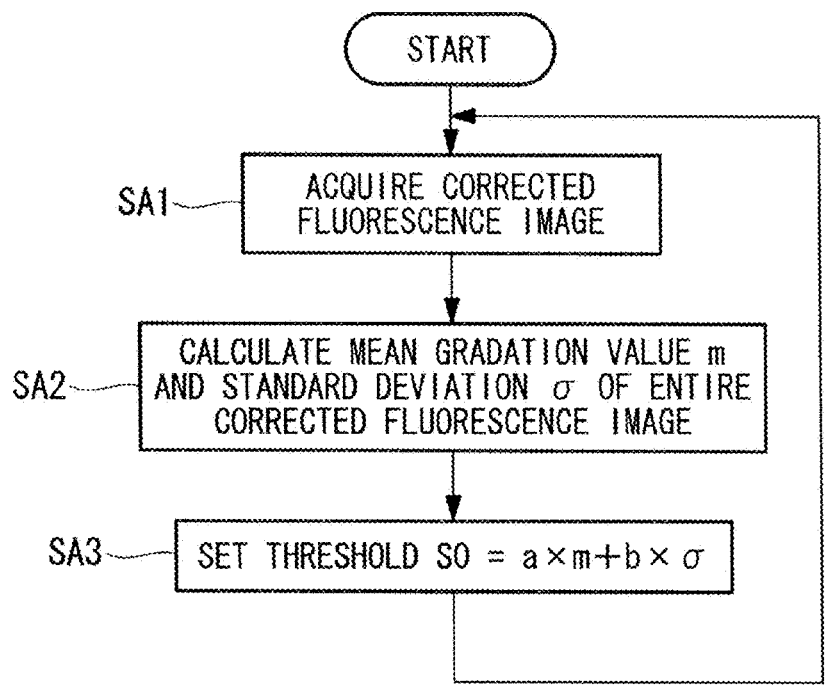
FIG. 2 is a flowchart for explaining setting of a threshold.

Threshold setting performed by the threshold setting part 45 will be described below with reference to a flowchart shown in FIG. 2.

Upon receiving the corrected fluorescence image G3 sent from the image correction part 43 (Step SA1), the threshold setting part 45 calculates the average gradation value m and the standard deviation $\sigma$ of the entire corrected fluorescence image G3 (Step SA2).

Then, a threshold S0 is calculated with Equation (3) by using the calculated average gradation value m and standard deviation $\sigma$ of the entire corrected fluorescence image G3 and is set by the threshold setting part 45 (Step SA3). The set threshold S0 is input to the extraction part 47.

Figure 3:
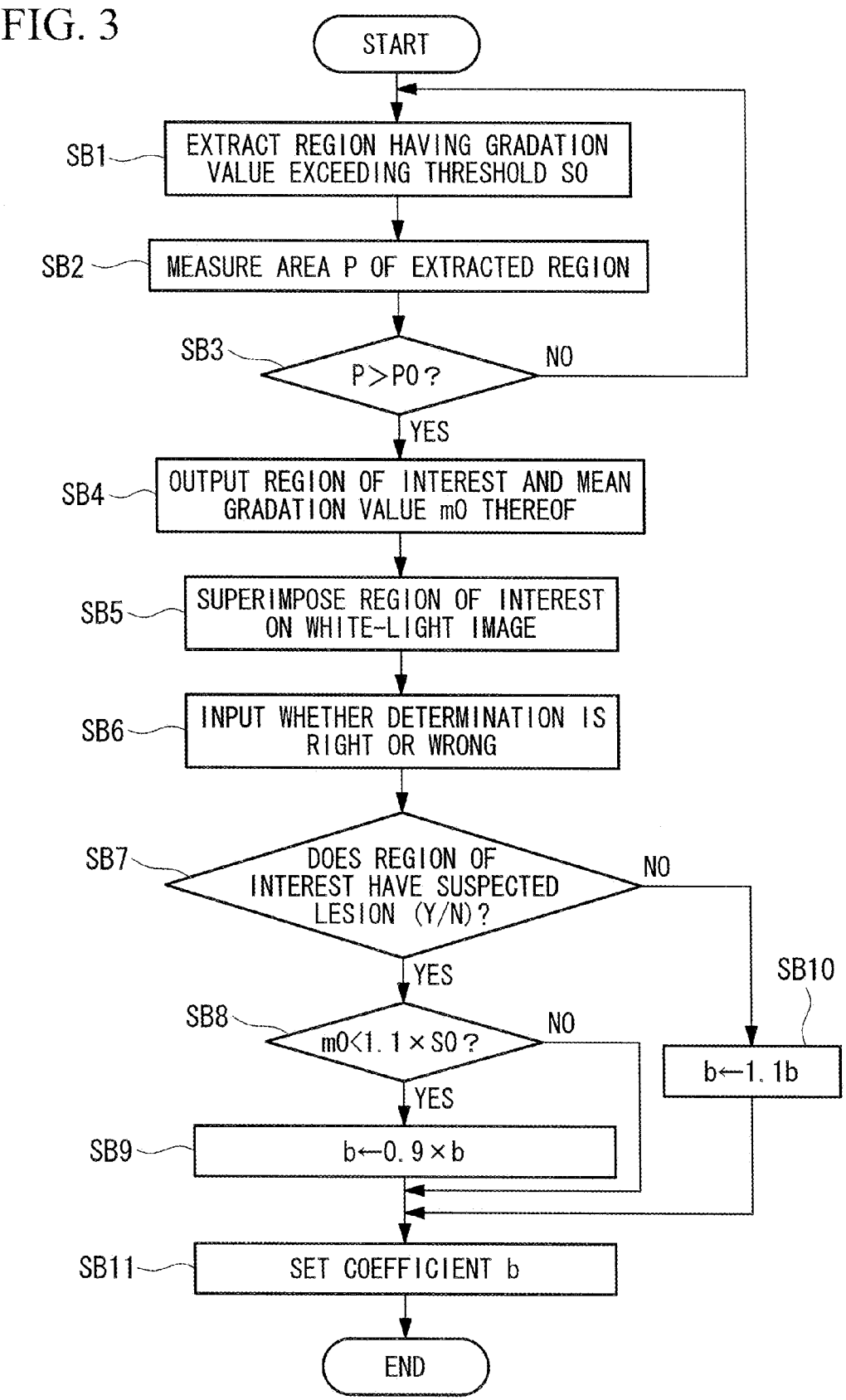
FIG. 3 is a flowchart for explaining setting of a coefficient for a standard deviation.

In this embodiment, the coefficient a in Equation (3) is set to 1 in advance. The coefficient b in Equation (3) for a first corrected fluorescence image G3 is set to 1, and the coefficient b in Equation (3) for second and subsequent corrected fluorescence images G3 is updated as needed, as indicated by a flowchart shown in FIG. 3.

First, the extraction part 47 extracts, from the corrected fluorescence image G3, a region that has a gradation value equal to or larger than a first threshold S0 (Step SB1).

The extraction part 47 measures the area (pixel count) P of the extracted region (Step SB2) and determines whether the area P is larger than the threshold P0 (Step SB3).

If the area P is equal to or smaller than the threshold P0 (Step SB3 "NO"), the flow returns to Step SB1. Thus, it is possible to prevent a situation in which a region (noise etc.) whose gradation value is high but whose area is small is extracted as a region of interest. Therefore, it is possible to suppress false extraction caused by noise, thus efficiently extracting a region of interest.

On the other hand, if the area P is larger than the threshold P0 (Step SB3 "YES"), the extraction part 47 determines the extracted region to be a region of interest and sends information about the region of interest to the threshold setting part 45 and the image compositing part 49. The extraction part 47 calculates the average gradation value m0 of the region of interest and sends it to the threshold setting part 45 (Step SB4).

Figure 4:
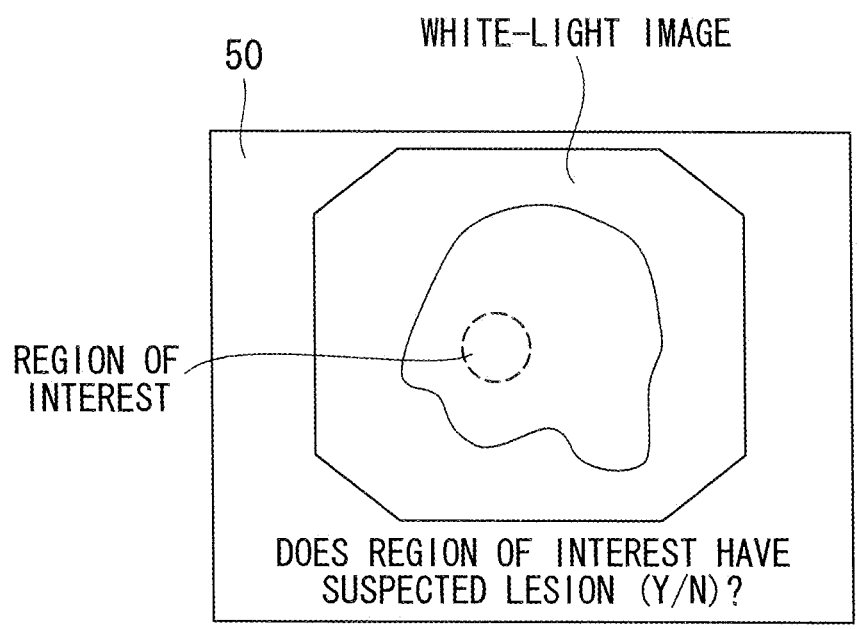
FIG. 4 is a view showing an example superimposed image and an example selection message for urging an observer to determine whether extraction performed by an extraction part is right, which are displayed on a monitor of the fluorescence observation device shown in FIG. 1.

Next, the image compositing part 49 superimposes, on the white-light image G2, the corrected fluorescence image G3 from which the background other than the region of interest has been removed (Step SB5), thus generating a superimposed image G4. Then, the superimposed image G4 is sent to the monitor 50, and the superimposed image G4 and a selection message for urging the observer to perform input are simultaneously displayed on the monitor 50, as shown in FIG. 4.

When the region of interest and the white-light image G2 are superimposed and displayed on the monitor 50, the observer can grasp the correspondence relationship between the region of interest and the white-light image G2 at a glance and can observe not only the region of interest but also an area around the region of interest. Therefore, the observer can acquire more detailed information and can more accurately determine whether the determination result given by the extraction part 47 is right.

While observing the superimposed image G4 displayed on the monitor 50, the observer determines whether the displayed region of interest has a suspected lesion and inputs a determination result to the input section 53 (Step SB6). In short, whether determination result of the region of interest extracted by the extraction part 47 was right or not is confirmed by the observer's input. Then, the determination result input through the input section 53 is input to the threshold setting part 45.

When the determination result given by the observer is input through the input section 53, the threshold setting part 45 updates the coefficient b so as to reflect this input result.

Specifically, if the determination input to the input section 53 is a Y determination (Step SB7 "YES"), the threshold setting part 45 determines whether m0<1.1×S0 is established, by using the average gradation value m0 of the region of interest and the upper threshold (1.1×S0), which is higher than the current threshold S0 by the predetermined rate (Step SB8).

If m0<1.1×S0 is established, the threshold setting part 45 updates the coefficient b to the value obtained by 0.9×b (Step SB9) and sets it as a new coefficient b (Step SB11).

When the difference between the average gradation value m0 of the region of interest and the threshold S0 is small, there is a possibility that a region having a gradation value smaller than the threshold S0 should be extracted as a region of interest, in subsequent rounds of extraction. Therefore, if m0<1.1×S0 is established, the coefficient b is reduced to reduce the threshold S0, thereby making it possible to extract a region having a gradation value smaller than the current threshold S0 as a region of interest in the next round of region-of-interest extraction, which prevents a necessary region of interest from being overlooked.

In other words, because the region of interest extracted based on the high threshold S0 that has not been updated has a suspected lesion, by reducing the threshold S0, it is possible to extract a region with a suspected lesion that has an even smaller gradation value, in the next round of extraction performed by the extraction part 47, and to improve the accuracy of diagnosis by preventing an oversight.

If m0≥1.1×S0 is established, the threshold setting part 45 maintains the value of the coefficient b as it is (Step SB11).

When the difference between the average gradation value m0 of the region of interest and the threshold S0 is sufficiently large, there is a high possibility that the threshold S0 is appropriate, and a necessary region of interest will be extracted, without being overlooked, in the next round of region-of-interest extraction, as well.

In this way, by setting the upper threshold (in this embodiment, 1.1×S0), the coefficient b can be maintained or reduced within the range of a predetermined rate (in this embodiment, 0.1) for the threshold S0, according to the circumstances. Therefore, the predetermined rate for the threshold S0, by which the upper threshold is set, is selected appropriately, thereby making it possible to efficiently extract a region of interest while preventing overlooking of a region of interest for which observation is necessary.

On the other hand, if the determination input to the input section 53 is an N determination (Step SB7 "NO"), the coefficient b is updated to the value obtained by 1.1×b (Step SB10), and the value is set as a new coefficient b (Step SB11).

There is a low possibility that a region having a gradation value equal to or smaller than the threshold S0 used to extract a region of interest should be extracted as a region of interest, in the next and subsequent rounds of extraction, as well. In other words, because a region extracted based on the low threshold S0 that has not been updated has no suspected lesion, by increasing the threshold S0, it is possible to avoid a fruitless situation in which a region with no lesion is wrongly extracted as a region of interest, in the next round of extraction performed by the extraction part 23, thus allowing an efficient diagnosis.

As described above, according to the fluorescence observation device 100 of this embodiment, the determination result given by the observer is used to update, for each corrected fluorescence image G3, the coefficient b for the standard deviation σ, which is used to determine the threshold S0 for extracting a region of interest, and the threshold S0 is set for each corrected fluorescence image G3. Thus, it is possible to acquire quantitative information about the object, in which errors in correcting the influence of the observation distance and the observation angle have been reduced.

Here, the average gradation value m0 of the region of interest is calculated by Equation (4).

$$m0 = a \times m + b0 \times \sigma \qquad (4)$$

In Equation (4), b0 indicates a coefficient (third coefficient).

From Equation (4), the coefficient b0 is calculated by Equation (5).

$$b0 = (m0 - a \times m)/\sigma \qquad (5)$$

Figure 5:
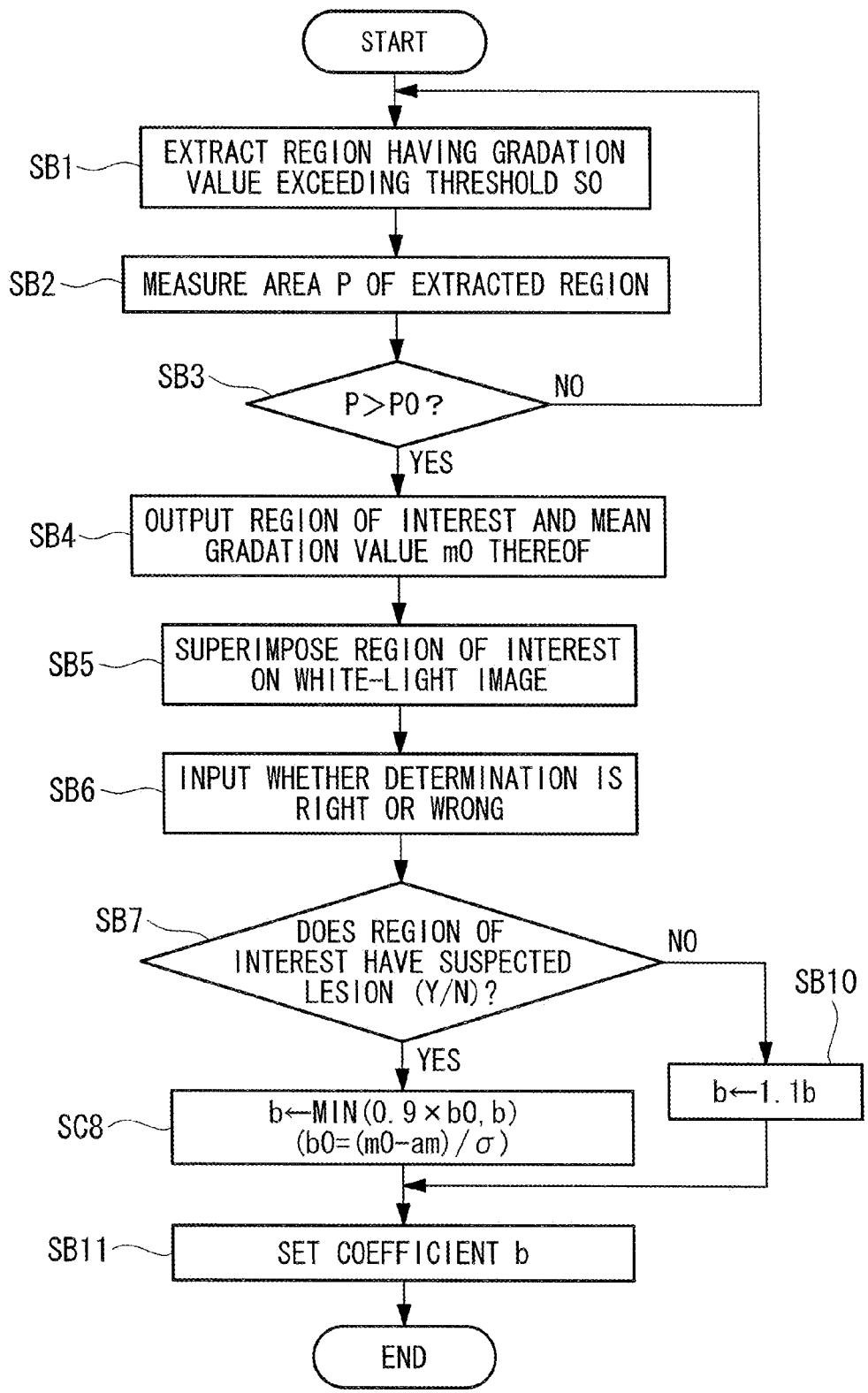
FIG. 5 is a flowchart for explaining setting of a coefficient for a standard deviation used in a fluorescence observation device according to a modification of the first embodiment of the present invention.

Therefore, in this embodiment, if the determination result input through the input section 53 is a Y determination, when $m0<1.1\times S0$ is established, the coefficient b is updated to the value obtained by $0.9\times b$; however, instead of this, when $m0<1.1\times S0$ is established, the coefficient b may be updated by using Equation (6). Specifically, as in Step SC8 in a flow-chart shown in FIG. 5, the value obtained by $0.9\times b0$ is compared with b, and the smaller value may be set as a new coefficient.

$$\mathrm{MIN}(0.9\times b0, b) \tag{6}$$

In this embodiment, although a description has been given of an example case in which the coefficient a is set to 1, the value of the coefficient a may be changed according to the observation state. In this embodiment, the value of the coefficient a is fixed, and the value of the coefficient b is updated; however, by using a similar method, it is possible to adopt a configuration in which the value of the coefficient a is updated, and the value of the coefficient b is fixed, or a configuration in which both the value of the coefficient a and the value of the coefficient b are updated. In this embodiment, although the threshold S0 is set based on the sum of the average gradation value m and the standard deviation σ of the entire corrected fluorescence image G3, the threshold S0 may be set by using one of the average gradation value m and the standard deviation σ of the entire corrected fluorescence image G3.

Second Embodiment

Next, a fluorescence observation device according to a second embodiment of the present invention will be described.

Figure 6:
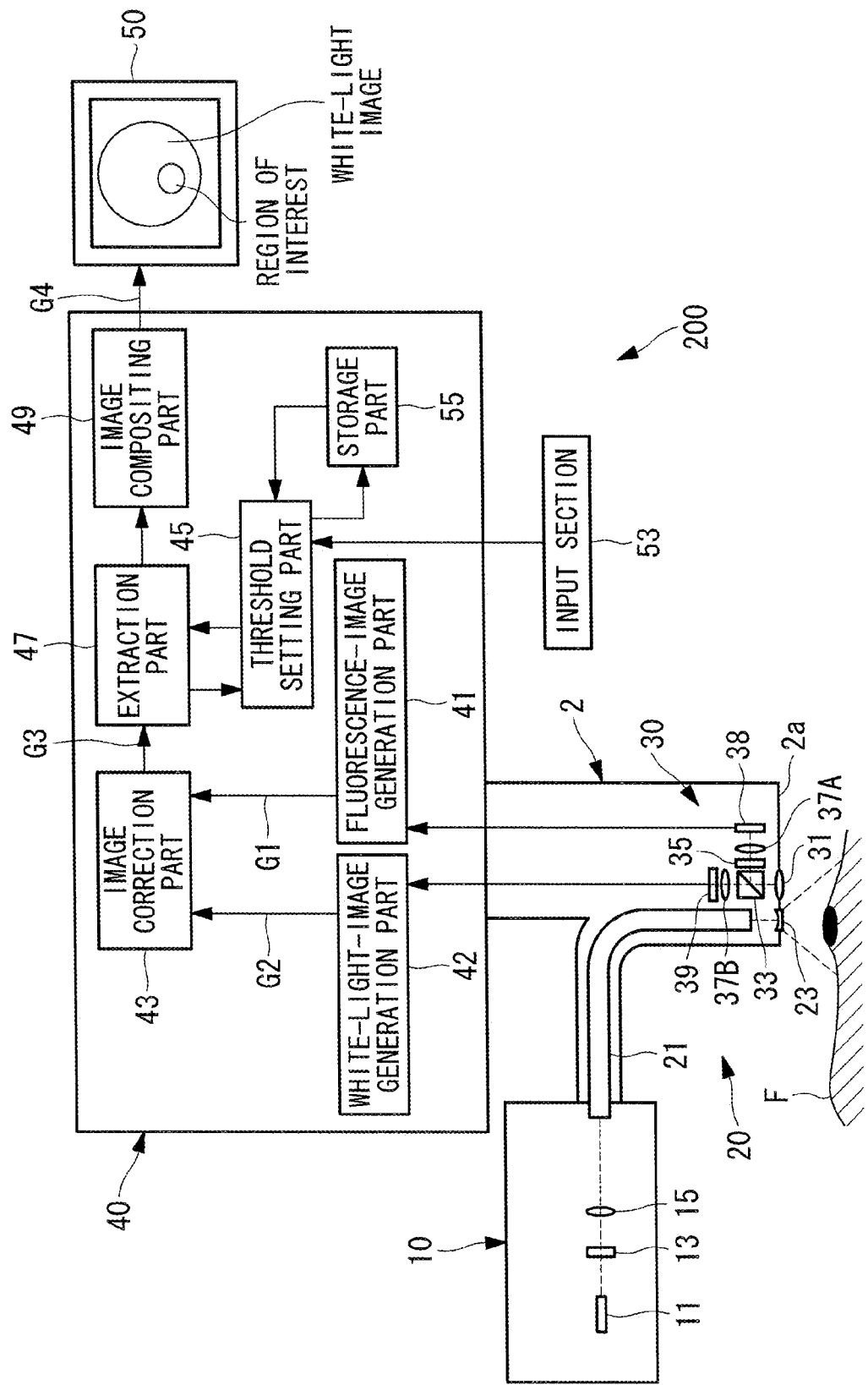
FIG. 6 is a configuration diagram showing, in outline, a fluorescence observation device according to a second embodiment of the present invention.

As shown in FIG. 6, a fluorescence observation device 200 according to this embodiment differs from that of the first embodiment in that the image processing section 40 includes a storage part 55, and the threshold S0 is set according to the average of previous coefficients a or b and the corresponding determination input result.

In the following description, identical reference symbols are assigned to the same components as those of the fluorescence observation device 100 of the first embodiment, and a description thereof will be omitted.

In this embodiment, the coefficient a is fixed to 1, and the coefficient b is updated, as needed.

When a region of interest is extracted by the extraction part 47, and a determination of the region of interest made by the observer is input through the input section 53, the storage part 55 stores a set of the average gradation value m0 of the region of interest, the threshold S0, the average gradation value m and the standard deviation σ of the corrected fluorescence image G3, the coefficients a and b, and the coefficient b0, in association with that determination result. For example, the storage part 55 stores these values in the form of the data shown in FIG. 7.

When a determination of a new region of interest made by the observer is input, the threshold setting part 45 reads all previous coefficients b0 that are stored in the storage part 55 in association with that input determination result and updates the coefficient b as follows.

For example, when a Y determination is input by the observer, the threshold setting part 45 calculates the average value AVE_Y(b0) of coefficients b0 that are set at all previous times the Y determination is input and that are read from the storage part 55 and updates the coefficient b by using Equation (7), with respect to the average value AVE_Y(b0).

Specifically, the threshold setting part 45 compares the value of $0.9\times \mathrm{AVE}\_Y(b0)$, which is a lower coefficient that is lower than the calculated average value AVE_Y(b0) of the coefficients b0 by a predetermined rate, with the value of the current coefficient b and sets the smaller of the values as a new coefficient b.

$$\mathrm{MIN}(0.9\times\mathrm{AVE}\_Y(b0), b) \tag{7}$$

In Equation (7), AVE_Y(b0) indicates the average value of coefficients b0 that are set at previous times the Y determination is input.

On the other hand, when an N determination is input by the observer, the threshold setting part 45 calculates the average value AVE_N(b0) of coefficients b0 that are set at all previous times the N determination is input and that are read from the storage part 55 and sets the average value AVE_N(b0) as a new coefficient b.

Thus, the coefficient b is changed, as shown in FIG. 8.

According to the fluorescence observation device 200 of this embodiment, a new threshold S0 can be set with the coefficient b, which reflects not only the latest determination result but also the previous determination results. In this case, by setting, as a new coefficient b, the smaller of the value obtained by $0.9\times \mathrm{AVE}\_Y(b0)$, which is a lower coefficient that is lower than the average value AVE_Y(b0) of the previous coefficients b0 stored in the storage part 55 by a predetermined rate, and the value of the current coefficient b, it is possible to more accurately extract a region with a suspected lesion.

If the determination made by the extraction part 47 is wrong, a new threshold S0 is set with the average value AVE_N(b0) of coefficients b0 that are set at previous times the wrong determination is made, thereby making it possible to prevent a fruitless situation in which a region for which observation is unnecessary is extracted as a region of interest, thus efficiently extracting a region of interest.

This embodiment can be modified as follows.

For example, as a first modification, in response to an input determination result, the threshold setting part 45 may calculate a standard deviation SD(b0) of coefficients b0 that are set at all previous times the Y determination is input and that are stored in the storage part 55. Then, the threshold setting part 45 may subtract the calculated standard deviation SD(b0) of the previous coefficients b0 from the average value AVE_Y (b0) of coefficients b0 that are set at all previous times the Y determination is input and may set, as a new coefficient b, the smaller of the value of AVE_Y(b0)−SD(b0), which is a lower coefficient obtained after the subtraction, and the value of the current coefficient b.

By doing so, the coefficient b is updated while taking into account variations among subjects, temporal variations in the same subject, and variations in the determination input from the observer, thus making it possible to set the threshold S0 more appropriately.

For example, when the sensitivity (not to overlook a lesion) is emphasized, a new threshold S0 may be set by MIN(AVE_Y(b0)−3×SD(b0), b) at the time of the Y determination. When the specificity (not to extract portions other than a lesion) is emphasized, a new threshold S0 may be set by MIN(AVE_Y(b0)−1×SD(b0), b) at the time of the Y determination.

In this way, there is the advantage that the coefficients (in this modification, a coefficient of 3 and a coefficient of 1) for SD(b0) are changed as desired, thereby making it possible to set the threshold S0 appropriately for an examination purpose.

As a second modification, the image processing section 40 may include a storing part (not shown) that receives the average gradation value m0 of a region of interest calculated by the extraction part 47 and information about a previous determination result input through the input section 8 and stores them in association with each other. The monitor 50 may read, for each region of interest, information about the previous determination result associated with the average gradation value m0 of that region, from the storing part, and display the information.

By doing so, when the observer determines whether the determination result made by the extraction part is right or not, the observer can refer to the previous determination result displayed on the monitor 50. As a result, the observer can make an accurate determination.

In the above-described embodiment, although a description has been given of an example case in which the coefficient a is fixed to 1, the value of the coefficient a can be changed according to the observation state. In that case, as the third coefficient, instead of the coefficient b0, a coefficient a0 can be calculated based on Equation (8), thus changing the value of the coefficient a.

$$a0 = (m0 - b \times \sigma)/m \qquad (8)$$

In Equation (8), a0 indicates a coefficient (third coefficient).

In the above-described embodiment, the value of the coefficient a is fixed, and the value of the coefficient b is updated; however, by using a similar method, it is also possible to adopt a configuration in which the value of the coefficient a is updated, and the value of the coefficient b is fixed, or a configuration in which both the value of the coefficient a and the value of the coefficient b are updated. It is also possible to calculate a standard deviation SD(a0) of coefficients a0 that are set at all previous times the Y determination is input and to set, as a new coefficient a, the smaller of the value of AVE_Y (a0)−SD(a0), which is a lower coefficient, and the value of the current coefficient a. The threshold S0 can also be set by using one of the average gradation value m and the standard deviation σ of the entire corrected fluorescence image G3.

Although the embodiments of the present invention have been described above in detail with reference to the drawings, the specific configuration is not limited to the embodiments, and design changes made without departing from the scope of the present invention are also encompassed. For example, the present invention is not limited to those applied to the above-described embodiments and modifications; it may be applied to an embodiment in which these embodiments and modifications are appropriately combined and is not particularly limited.

In the above-described embodiments, although the region of interest in the corrected fluorescence image G3 is superimposed on the white-light image G2 by the image compositing part 49 and is then displayed on the monitor 50, the corrected fluorescence image G3 and the white-light image G2 may be displayed on the monitor 50 side by side. At this time, the region of interest may be outlined and displayed in the corrected fluorescence image G3. By doing so, it is possible to provide the observer with more detailed information and to allow the observer to make a more accurate determination, compared with a case in which only the region of interest extracted based on the threshold S0 is displayed.

In the above-described embodiments, the extraction part 47 may extract two different regions that have gradation values equal to or larger than the threshold and display the regions on the monitor 50 by different display methods. For example, the extraction part 47 may extract a region whose average gradation value m0 of the region of interest exceeds the threshold S0 and a region whose average gradation value m0 of the region of interest exceeds 80% of the threshold S0, for example.

In the above-described embodiments, although the extraction part 47 calculates the average gradation value m0 of the region of interest, the extraction part 47 may calculate another value. For example, the minimum gradation value in the region of interest may be calculated, or the maximum gradation value in the region of interest may be calculated.

When there are a plurality of regions of interest extracted by the extraction part 47 on the same screen, the image compositing part 49 may generate a superimposed image G4 in which only a region of interest to be subjected to a determination is displayed in a different way from the other regions of interest, so that the observer can clearly know for which region of interest the observer should input a right/wrong determination. In order to distinguish that region of interest from the other regions of interest, it is possible to generate a superimposed image G4 in which only the region of interest to be subjected to a determination is flashed, and the other regions of interest are turned on, for example.

In this case, it is possible to set a determination order for the plurality of regions of interest and to flash the display of only a region of interest to be subjected to a determination according to the set order. In order to prevent a determination from being redundantly input, a region of interest for which a determination has already been input can be displayed so as to show that the determination has been input for the region of interest; for example, it can be displayed in a different color.

REFERENCE SIGNS LIST

10 light source (illumination section)
20 illumination unit (illumination section)
41 fluorescence-image generation part (fluorescence-image acquisition part)
42 white-light-image generation part (reference-image acquisition part)
43 image correction part (corrected-fluorescence-image generation part)
45 threshold setting part
47 extraction part
50 monitor (display section)
53 input section (right/wrong input section)
55 storage part
100, 200 fluorescence observation device
a coefficient (first coefficient)
b coefficient (first coefficient)
b0 coefficient (third coefficient)
m0 the average of gradation values of an extracted region
S0 threshold (gradation-value threshold)

The invention claimed is:
1. A fluorescence observation device comprising:
a light source configured to radiate excitation light and reference light onto an object;
a fluorescence capturing sensor configured to capture fluorescence produced in the object irradiated with the excitation light;
a return light capturing sensor configured to capture return light from the object irradiated with the reference light; and
a processor comprising hardware, wherein the processor is configured to:
generate a fluorescence image based on the fluorescence captured by the fluorescence capturing sensor;
generate a reference image based on the return light captured by the return light capturing sensor;
generate a corrected fluorescence image by correcting the fluorescence image with the reference image;

set a gradation-value threshold based on an average of gradation values of the entire corrected fluorescence image, a standard deviation of the gradation values, a first coefficient related to weighting of the average of the gradation values of the entire corrected fluorescence image, and a second coefficient related to weighting of the standard deviation of the gradation values;

determine and extract, as a candidate region of interest, a region in the corrected fluorescence image that has a gradation value larger than the gradation-value threshold;

control a display to display the candidate region of interest extracted and the reference image in association with each other; and receive a result, inputted by an observer, as to whether the candidate region of interest displayed on the display is right or wrong, wherein a result of right indicates a determination by the observer that the candidate region of interest is a region of interest, and a result of wrong indicates a determination by the observer that the candidate region of interest is not a region of interest, wherein the processor is configured to set at least one of the first coefficient and the second coefficient so as to reflect the result inputted by the observer.

2. The fluorescence observation device according to claim 1,
wherein the processor is configured to correct the fluorescence image with the reference image by dividing the fluorescence image by the reference image.

3. The fluorescence observation device according to claim 1,
wherein the processor is configured to set one of the first coefficient and the second coefficient to a fixed value and maintain or reduce the other of the first coefficient and the second coefficient in response to receiving the result of right.

4. The fluorescence observation device according to claim 3,
wherein the processor is configured to maintain the other of the first coefficient and the second coefficient in response to the gradation value of the candidate region of interest being larger than an upper gradation-value threshold that is higher than the gradation-value threshold by a predetermined rate and reduce the other of the first coefficient and the second coefficient in response to the gradation value of the candidate region of interest being lower than the upper gradation-value threshold.

5. The fluorescence observation device according to claim 1,
wherein the processor is configured to set one of the first coefficient and the second coefficient to a fixed value and to increase the other of the first coefficient and the second coefficient in response to receiving the result of wrong.

6. The fluorescence observation device according to claim 1,
wherein the processor is configured to calculate the gradation-value threshold by the following equation:

$$S0 = a \times m + b \times \sigma$$

where S0 indicates the gradation-value threshold,
a indicates the first coefficient,
b indicates the second coefficient,
m indicates the average of the gradation values of the entire corrected fluorescence image, and
σ indicates the standard deviation of the gradation values of the entire corrected fluorescence image.

7. The fluorescence observation device according to claim 1,
wherein the processor is configured to:
calculate an average of gradation values of the extracted region; and
calculate a third coefficient based on the average of the gradation values of the extracted region;
wherein the fluorescence observation device further comprises a storage configured to store, in response to the candidate region of interest being extracted and receiving the result inputted by the observer, the result inputted by the observer and the third coefficient in association with each other; and
wherein in response to receiving the result of right for a new candidate region of interest, the processor is configured to set, as a new first coefficient, the smaller of the current first coefficient and a lower coefficient that is lower, by a predetermined rate, than an average value of previous third coefficients stored in the storage in association with the received result.

8. The fluorescence observation device according to claim 1,
wherein the processor is configured to:
calculate an average of gradation values of the extracted region, and
calculate a third coefficient based on the average of the gradation values of the extracted region;
wherein the fluorescence observation device further comprises a storage configured to store, in response to the candidate region of interest being extracted and receiving the result of right inputted by the observer, the result of right and the third coefficient in association with each other, and
wherein in response to receiving a result of right for a new candidate region of interest, the processor is configured to set as a new second coefficient, the smaller of the current second coefficient and a lower coefficient that is lower, by a predetermined rate, than an average value of previous third coefficients stored in the storage in association with the received result.

9. The fluorescence observation device according to claim 1,
wherein the processor is configured to:
calculate an average of gradation values of the candidate region of interest; and
calculate a third coefficient based on the average of the gradation values of the candidate region of interest,
wherein the fluorescence observation device further comprises a storage configured to store, in response to the candidate region of interest being extracted and receiving the result inputted by the observer, the result and the third coefficient in association with each other, and
wherein in response to receiving a result of right indicating that a new candidate region of interest the processor is configured to calculate a standard deviation of the previous third coefficients stored in the storage in association with the received result and set, as a new first coefficient, the smaller of the current first coefficient and a lower coefficient that is obtained by subtracting the calculated standard deviation of the third coefficients from an average value of the previous third coefficients stored in the storage.

10. The fluorescence observation device according to claim 1,
   wherein the processor is configured to:
      calculate an average of gradation values of the extracted region; and
      calculate a third coefficient based on the average of the gradation values of the extracted region;
   wherein the fluorescence observation device further comprises a storage configured to store, in response to the candidate region of interest being extracted and receiving the result inputted by the observer, the result inputted by the observer and the third coefficient in association with each other, and
   wherein, in response to receiving a result of right for a new candidate region of interest, the processor is configured to calculate a standard deviation of the previous third coefficients stored in the storage in association with the received result and set, as a new second coefficient, the smaller of the current second coefficient and a lower coefficient that is obtained by subtracting the calculated standard deviation of the third coefficients from an average value of the previous third coefficients stored in the storage.

11. The fluorescence observation device according to claim 7, wherein, in response to receiving the result of wrong, the processor is configured to set, as a new first coefficient, the average value of the previous third coefficients stored in the storage in association with the received result.

12. The fluorescence observation device according to claim 8,
   wherein, in response to receiving a result of wrong, the processor is configured to set, as a new second coefficient, the average value of the previous third coefficients stored in the storage in association with the received result.

13. The fluorescence observation device according to claim 7, wherein the processor is configured to calculate the third coefficient by the following equation:

$$a0=(m0-b\times\sigma)/m$$

where a0 indicates the third coefficient,
   m0 indicates the average of the gradation values of the extracted region,
   b indicates the second coefficient,
   σ indicates the standard deviation of the gradation values of the entire corrected fluorescence image, and
   m indicates the average of the gradation values of the entire corrected fluorescence image.

14. The fluorescence observation device according to claim 8, wherein the processor is configured to calculate the third coefficient by the following equation:

$$b0=(m0-a\times m)/\sigma$$

where b0 indicates the third coefficient,
   m0 indicates the average of the gradation values of the extracted region,
   a indicates the first coefficient,
   m indicates the average of the gradation values of the entire corrected fluorescence image, and
   σ indicates the standard deviation of the gradation values of the entire corrected fluorescence image.

15. The fluorescence observation device according to claim 1,
   wherein the processor is configured to control the display the candidate region of interest and the reference image in association with each other by displaying the candidate region of interest and the reference image in a superimposed manner.

16. The fluorescence observation device according to claim 1,
   wherein the processor is configured to extract, as the candidate region of interest, a region whose pixel count is larger than a pixel count threshold among regions that have gradation values exceeding the gradation-value threshold.

17. The fluorescence observation device according to claim 1, further comprising a storage configured to store the gradation value of the candidate region of interest and information about a previous determination result, in association with each other,
   wherein the processor is configured to:
      read, for each candidate region of interest, the information about the previous determination result associated with the gradation value of that candidate region of interest from the storage; and
      display the information.

18. The fluorescence observation device according to claim 9,
   wherein, in response to receiving the result of wrong, the processor is configured to set, as a new first coefficient, the average value of the previous third coefficients stored in the storage in association with the received result.

19. The fluorescence observation device according to claim 10,
   wherein, in response to receiving the result of wrong, the processor is configured to set, as a new second coefficient, the average value of the previous third coefficients stored in the storage in association with the received result.

20. The fluorescence observation device according to claim 9, wherein the processor is configured to calculate the third coefficient by the following equation:

$$a0=(m0-b\times\sigma)/m$$

where a0 indicates the third coefficient,
   m0 indicates the average of the gradation values of the extracted region,
   b indicates the second coefficient,
   σ indicates the standard deviation of the gradation values of the entire corrected fluorescence image, and
   m indicates the average of the gradation values of the entire corrected fluorescence image.

21. The fluorescence observation device according to claim 11, wherein the processor is configued to calculate the third coefficient by the following equation:

$$a0=(m0-b\times\sigma)/m$$

where a0 indicates the third coefficient,
   m0 indicates the average of the gradation values of the extracted region,
   b indicates the second coefficient,
   σ indicates the standard deviation of the gradation values of the entire corrected fluorescence image, and
   m indicates the average of the gradation values of the entire corrected fluorescence image.

22. The fluorescence observation device according to claim 10, wherein the processor is configured to calculate the third coefficient by the following equation:

$$b0=(m0-a\times m)/\sigma$$

where b0 indicates the third coefficient, m0 indicates the average of the gradation values of the extracted region, a indicates the first coefficient, m indicates the average of the gradation values of the entire corrected fluorescence image, and σ indicates the standard deviation of the gradation values of the entire corrected fluorescence image.

23. The fluorescence observation device according to claim 12, wherein the processor is configured to calculate the third coefficient by the following equation:

$$b0 = (m0 - a \times m)/\sigma$$

where b0 indicates the third coefficient, m0 indicates the average of the gradation values of the extracted region, a indicates the first coefficient, m indicates the average of the gradation values of the entire corrected fluorescence image, and σ indicates the standard deviation of the gradation values of the entire corrected fluorescence image.

\* \* \* \* \*